(12) United States Patent
Wells et al.

(10) Patent No.: US 8,317,989 B2
(45) Date of Patent: *Nov. 27, 2012

(54) ELECTROCHEMICAL SENSOR

(75) Inventors: Steven Wells, Huntington Beach, CA (US); Gert Burkhardt, Pasadena, CA (US); Anthony Thai, Orange, CA (US)

(73) Assignee: Georg Fischer Signet LLC, El Monte, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/008,839

(22) Filed: Jan. 18, 2011

(65) Prior Publication Data

US 2011/0114484 A1 May 19, 2011

Related U.S. Application Data

(63) Continuation of application No. 11/564,015, filed on Nov. 28, 2006, now Pat. No. 7,909,972.

(51) Int. Cl.
*G01N 27/30* (2006.01)
(52) U.S. Cl. ...... 204/433; 204/435; 204/409; 205/787.5
(58) Field of Classification Search .......... 204/409–420, 204/433, 435; 205/787.5, 789, 789.5, 793
See application file for complete search history.

(56) References Cited

U.S. PATENT DOCUMENTS

| 4,112,352 A | 9/1978 | Barben |
| 4,128,468 A | 12/1978 | Bukamier |
| 4,235,688 A | 11/1980 | Sudrabin et al. |
| 5,145,565 A | 9/1992 | Kater |
| 5,147,524 A | 9/1992 | Broadley |
| 5,152,882 A | 10/1992 | Benton |
| 5,346,606 A | 9/1994 | Christner et al. |
| 5,630,921 A | 5/1997 | Hess et al. |
| 6,054,031 A | 4/2000 | Benton |
| 6,416,653 B1 | 7/2002 | Barben, II et al. |
| 6,423,197 B1 | 7/2002 | Lenferink et al. |
| 2002/0043095 A1 | 4/2002 | Mason et al. |
| 2004/0195098 A1 | 10/2004 | Broadley et al. |

OTHER PUBLICATIONS

"pH Theory and Measurement", *Barben Analyzer Technology, LLC*, Carson City, NV (earlier than Jun. 2006), pp. 1-11.
"Sensor Evolution", *Barben Analyzer Technology, LLC*, Carson City, NV, 5 pages, (earlier than Jun. 2006), pp. 4-5.
Spiegler, K. S., "Determination of Resistance Factors of Porous Diaphragms and Electrodes", *Electrochemical Society*, vol. 113, No. 2, 0013-4651, (1966), pp. 161-165.

*Primary Examiner* — Kaj K Olsen
*Assistant Examiner* — Kourtney R Carlson
(74) *Attorney, Agent, or Firm* — Tsircou Law, P.C.

(57) ABSTRACT

An electrochemical sensor is provided that includes a housing having an outer wall, an axial bore circumscribed by the outer wall, and a barrier wall that aids in defining a reference cavity. The housing further including a plurality of cross members in spaced relation to one another disposed between the axial bore and the outer wall, each cross member defining an aperture. A junction plug is disposed at the distal end of the housing. The junction plug comprises a porous material that enables ionic flow through the junction plug. The sensor enables ionic communication between the target fluid and the reference electrode within the reference cavity through the apertures of the plurality of cross members. In this manner, the sensor provides generally a long, tortuous flow path, or salt bridge, between the target fluid and the reference electrode, resulting in a high resistance factor for the sensor.

20 Claims, 5 Drawing Sheets

ELECTROCHEMICAL SENSOR

CROSS REFERENCE TO RELATED APPLICATION

This application is a continuation application of U.S. application Ser. No. 11/564,015, filed Nov. 28, 2006, which is herein incorporated by reference.

FIELD OF THE INVENTION

The present invention relates generally to electrochemical sensors and, more particularly, to such sensors having a reference electrode and a measuring electrode for measuring parameters of a target fluid.

BACKGROUND OF THE INVENTION

Electrochemical sensors have long been used to measure properties of fluids. Such sensors typically include a measuring electrode assembly and a reference electrode assembly, both which are electrically coupled to an instrument that senses the difference in electrical potential between the electrodes. In sensors of this kind, the measuring electrode assembly typically is exposed directly to the target fluid; whereas the reference electrode assembly is immersed in a stable electrolytic solution, i.e., a reference electrolyte. Sensors of this kind further include an ion-permeable separator, commonly referred to as liquid junction or salt bridge, disposed between the reference electrolyte and the target fluid, to enable a closed circuit between the electrodes.

In use, the measuring electrode generates a potential that varies as a function of prescribed parameters of the target fluid. The potential difference between the measuring electrode and the reference electrode provides a basis for measuring the prescribed parameters of the target fluid. For an accurate reading, the reference electrode must provide a stable potential.

The liquid junction plays an important role in achieving and maintaining a stable potential for the reference electrode. Ideally, the liquid junction should enable ionic communication between the reference electrolyte and the target fluid, while otherwise preventing transfer or intermingling of the fluids. Contamination or dilution of the reference electrolyte can unduly inhibit performance of the reference electrode, which is of particular concern when used in harsh chemical environments. The ability of the liquid junction to inhibit diffusion of the measured fluid, and ions therefrom, can be generally referred to as its resistance factor.

Much attention has been given to designing effective liquid junctions having a high resistance factor. Many approaches attempt to establish a tortuous path for ions through the junction by confining travel through relatively complex structural configurations that incorporate multiple components assembled together. For example, certain approaches include multiple layers held together with wood dowels. Other approaches utilize long path salt bridges for ionic communication between the liquid junction and the reference electrode, which generally require such sensors to have a relatively large sensor body, including housing length and diameter. Current approaches particularly in industrial applications, often combine multiple tortuous path junctions connected by long path salt bridges.

Although generally effective, such approaches are relatively expensive and time-consuming to manufacture. Moreover, performance of such approaches can deteriorate with time.

It should be appreciated that there remains a need for an electrochemical sensor that addresses these concerns. The present invention fulfills this need and others.

SUMMARY OF THE INVENTION

In general terms, the present invention provides an electrochemical sensor comprising a housing having an outer wall, an axial bore circumscribed by the outer wall, and a barrier wall that aids in defining a reference cavity. The housing further including a plurality of cross members in spaced relation to one another disposed between the axial bore and the outer wall, each cross member defining an aperture. A junction plug is disposed at the distal end of the housing. The junction plug comprises a porous material that enables ionic flow through the junction plug. The sensor enables ionic communication between the target fluid and the reference electrode within the reference cavity passes through the apertures of the plurality of cross members. In this manner, the sensor provides generally a long, tortuous flow path, or salt bridge, between the target fluid and the reference electrode, resulting in a high resistance factor for the sensor.

In detail aspects of certain exemplary embodiments of the invention, the plurality of cross members are generally parallel to one another. The apertures of adjacent cross members are disposed on alternating sides from one another. In selected embodiments, the housing has an outer member including the outer wall and an inner member disposed within the outer member, the inner member including the axial bore and the plurality of cross members. The inner member of the housing is formed of molded plastic.

In other detail aspects of certain exemplary embodiments of the invention, the sensor further comprises an aperture plug formed of porous material disposed in at least one of the apertures defined by the plurality of cross members. More particularly, a plurality of aperture plugs formed of porous material are disposed in the apertures defined by the plurality of cross members. Also, the first cross member can be affixed to the second surface of the junction plug.

In yet other detailed aspects of certain exemplary embodiments of the invention, the housing can further include barriers extending between adjacent cross members. Apertures of the adjacent cross members are disposed on opposing sides of the barrier such that ions must travel substantially the full circumference of the housing between the adjacent apertures.

In a distinct aspect in accordance with the invention, a method of manufacturing an electrochemical sensor is provided, comprising the following steps:

providing a housing having an outer wall, an axial bore circumscribed by the outer wall, and a barrier wall that aids in defining a reference cavity, the housing further including a plurality of cross members in spaced relation to one another disposed between the axial bore and the outer wall, each cross member defining an aperture, the housing including a proximal end and a distal end configured to be proximate to a target fluid;

disposing a reference electrode within the cavity of the housing; and disposing a junction plug comprising porous material at a distal end of the housing the plug having a first surface configured to contact the target fluid and a second surface, the junction plug comprising a porous material that enables ionic flow through the junction plug from the first surface to the second surface; wherein ionic communication between the target fluid and the reference electrode within the reference cavity passes through the apertures of the plurality of cross members.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF THE PREFERRED EMBODIMENTS

Figure 1:
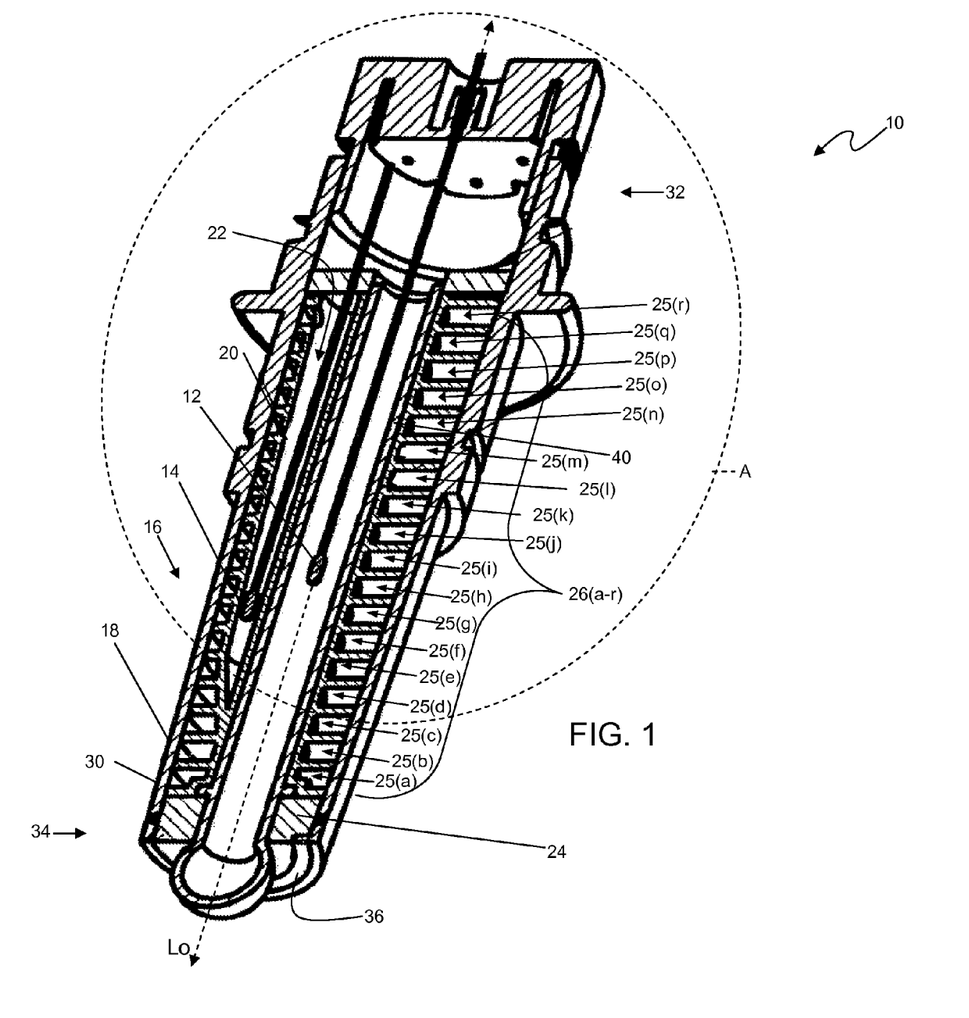
FIG. 1 is a cross-sectional view of a first embodiment of an electrochemical sensor in accordance with the present invention, depicting a reference electrode disposed within a cavity of a housing having an outer member and an inner member.
Figure 2:
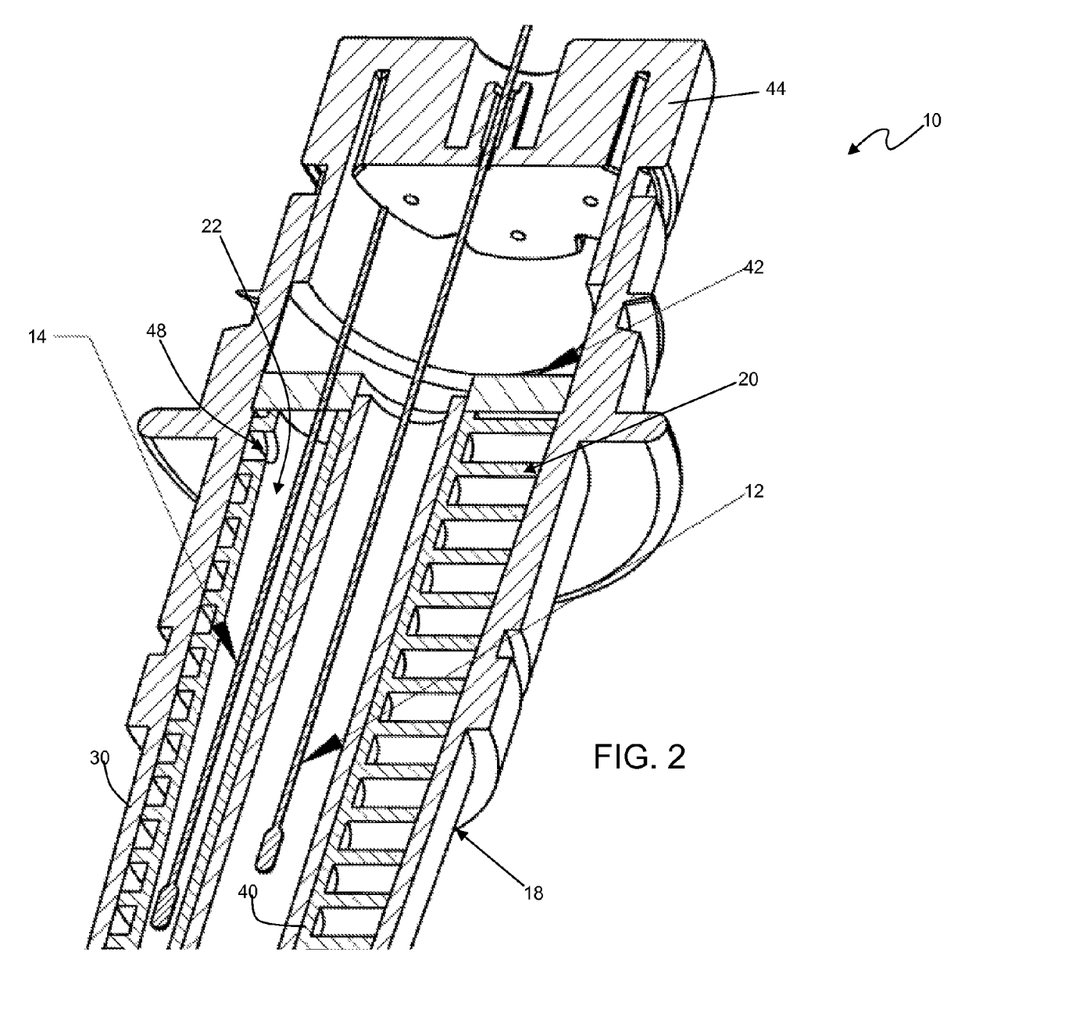
FIG. 2 is close-up, cross-sectional view of Area A of the electrochemical sensor of FIG. 1.

Referring now to the drawings, and particularly to FIGS. 1 and 2, there is shown an electrochemical sensor assembly 10, for measuring parameters of a target fluid (not shown), such as ORP or specific ions, e.g., pH or sodium. The sensor assembly 10 includes a measuring electrode 12 (e.g., glass pH electrode) and a reference electrode 14 coupled to a housing 16, having an outer member 18 and an inner member 20. The reference electrode is disposed within a reference cavity 22, defined by the inner member of the housing, and is surrounded by a reference electrolyte. The sensor assembly includes a liquid junction comprising a junction plug 24 disposed at distal end of the housing. The inner member includes a plurality of cross members 26($a$-$r$), each defining an aperture 28($a$-$r$). The cross members and apertures aid in defining a long, tortuous flow path, or salt bridge, between the target fluid and the reference electrode, resulting in a high resistance factor for the sensor.

Figure 3:
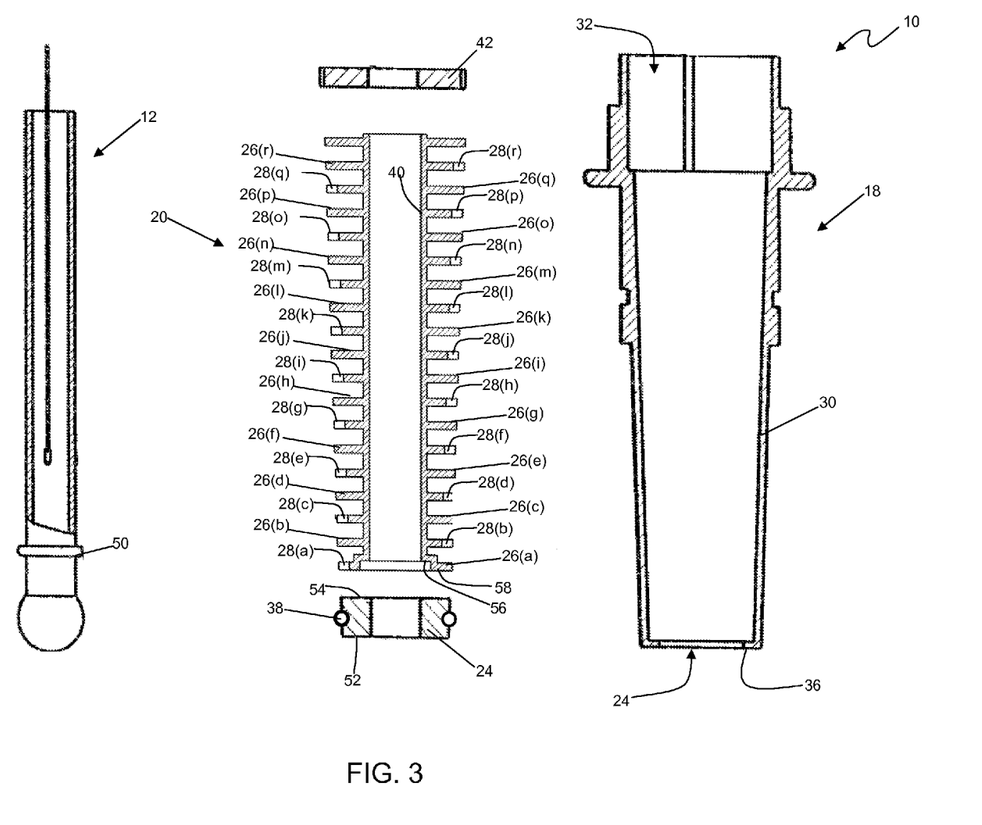
FIG. 3 is partially exploded view of the electrochemical sensor of FIG. 1, depicting selected components in cross section, including a cross-sectional view of the inner member of the housing taken along line 3-3 of FIG. 4.
Figure 4:
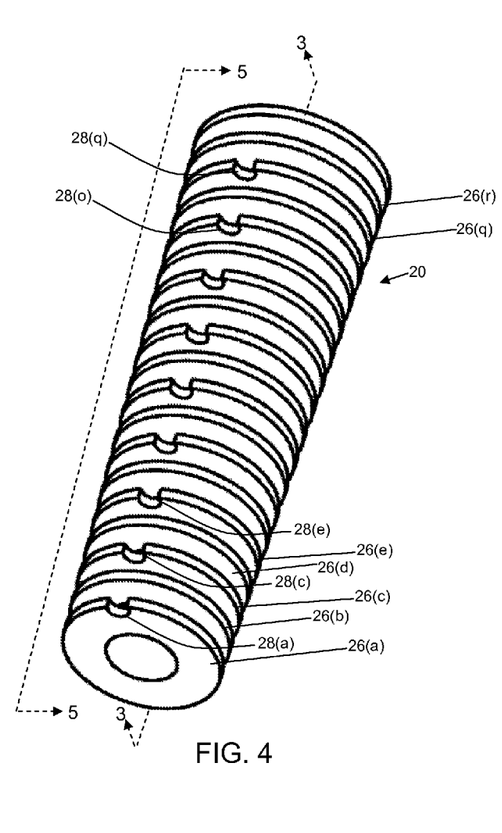
FIG. 4 is a perspective view of the inner member of the housing the electrochemical sensor of FIG. 1.

As best seen in FIG. 3, the apertures 28($a$-$r$) are aligned along a planar cross section of the inner member 20, taken along line 3-3 of FIG. 4. The apertures of adjacent cross members are disposed on alternating sides of the inner member 20 relative to a longitudinal axis ($L_o$) (FIG. 1) of the sensor assembly. For example, aperture 28($b$) is disposed on a first side of the inner member, whereas aperture 28$c$ is disposed on a second side of the inner member. The apertures 28($a$-$r$) alternate in this manner between the proximal end and the distal end, requiring ionic flow between the target fluid and the reference electrode 14 to traverse laterally and longitudinally through the housing. Thus, this configuration provides a relatively long flow path.

In the exemplary embodiment, the inner member 20 includes eighteen cross members 26 that define alternating apertures 28; however, various other numbers of cross members can be used, so long as ionic flow is maintained. The apertures 28 allow the reference electrolyte to flow among the levels 25($a$-$r$) between the cross members 26. In other embodiments, porous barriers, e.g., an aperture plugs, can be disposed in one or more of the apertures to retard contamination, while enabling ionic flow. Materials for such barriers include, for example, ground glass, ceramic, porous plastics, and wood. Such configurations can increase manufacturing costs but, nonetheless, can be beneficial in particularly harsh chemical environments.

With reference again to FIG. 1, the outer member 18 has a sidewall 30 and defines proximal and distal openings 32, 34, respectively. The outer member includes an inwardly facing flange 36 disposed about the distal opening. The flange is sized such that the junction plug 24 can be securely seated in place proximate to the distal opening to contact the target fluid. An o-ring 38 is disposed about the junction plug to engage the sidewall 30 of the outer member, providing a secure seal about the plug and ensuring ionic communication occurs through the tortuous path of the junction plug and not through micro gaps between the junction and the sidewall.

The inner member 20 of the housing 16 is coupled to and disposed within the outer member 18. The inner member includes a cylindrical bore 40 aligned with the longitudinal axis $L_o$ of the housing and configured to receive the measuring electrode 12. The sidewall 30 of the outer member 18 is generally equidistantly spaced from the bore about the circumference thereof and slopes inwardly from the proximal opening 32 to the distal opening 34.

With reference to FIG. 2, the sensor assembly 10 further includes an upper seal 42 and a cap 44 disposed atop the proximal opening 32 of the outer member 18. The upper seal is positioned above the inner member 20, and the upper seal is configured to engage the cylindrical bore 40 of the inner member and the sidewall 30 of the outer member 18 to provide a fluid tight seal, to confine the reference electrolyte.

Figure 5:
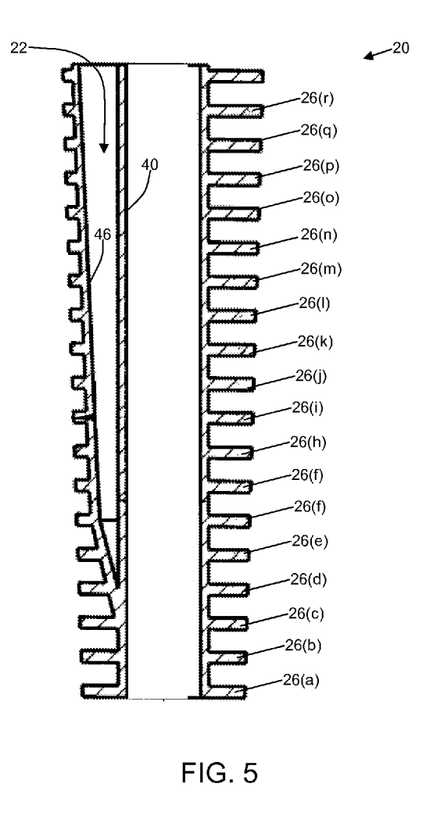
FIG. 5 is a cross-sectional view, taken along the line 5-5 of FIG. 4.

With reference now to FIG. 5, the inner member 20 further includes a barrier wall 46 that aids in defining the reference cavity 22. The barrier wall is disposed between the cylindrical bore 40 and several of the cross members 26, along a first side of the inner member. The barrier wall defines an opening 48, shown in FIG. 2, that enables access to the reference cavity from the cross member region, to facilitate ionic communication. The opening 48 is disposed adjacent to upper seal 42, such that ionic flow must traverse a substantial distance through each aperture 28 to reach the reverence cavity.

During assembly, the measuring electrode 12 is inserted into the junction plug 24. An o-ring 50 is put down over the back of the measuring electrode 12, fitting snugly against the plug 24. This combination and the inner member 20 are inserted through the proximal opening 32 of the outer member 18 of the housing. The inner member is sized such that the diameter of each of the cross members 26($a$-$r$) correspond to the inner diameter of the outer member at corresponding locations, to provide a secure seal. The upper seal 42 and the cap 44 are also positioned in place. Adhesive material can be provided to secure the various components, as needed. Nonetheless, care should be taken to ensure that the apertures 28(a-r) do not become blocked with material that would bar electrochemical communication between the target fluid and the reference electrode.

In other embodiments, the inner member can be coupled to the outer cylindrical member in such manner to enable disassembly for maintenance purposes. For example, the inner and outer members can couple via cooperative attachments or assemblies, e.g., threaded portions, tongue and groove engagements, and other suitable attachments.

In the exemplary embodiment, the outer and the inner members 18, 20, respectively, are formed of molded plastic, such as polypropylene, PP. In other embodiments, other materials can be used. Some examples of other material that can be used include polyphenylsulfone PPS, polyvinyl chloride PVC, chlorinated polyvinyl chloride CPVC, polyvinyldiflouride PVDF, or other materials known in the art having appropriate chemical resistivity for a particular application.

Although the housing configuration is discussed in detail to the exemplary embodiment having an inner and outer member, other configurations can be implemented without departing from the invention. For example, one or more cross members can be provided by the outer member. Also, the cross members can be provided by a component separate from the cylindrical bore.

The measuring electrode 12 and a reference electrode 14 are configured to be coupled to instrumentation, e.g., amplifier (not shown), to sense the potential difference between the measuring electrode and the reference electrode. The housing further includes a cap 44 received atop the proximal opening 46 of the outer member. Wires attached to the electrodes pass through the cap to couple to the instrumentation.

In use, the end portion of the measuring electrode 12 is exposed to the target fluid such that the measuring electrode is electrochemically coupled to the target fluid. In the exemplary embodiment, a sensor assembly is configured to detect pH (e.g., a glass pH electrode). However, other embodiments can be configured to measure other parameters, individual or in combination. For example, oxidation-reduction potential (ORP), using a nobel metal electrode, or other types of specific ions can be measured including, for example, ammonium, bromide, chloride, fluoride, sulfide, nitrate, and sodium.

The reference electrode 14 is not directly exposed to the target fluid; rather it is surrounded by a reference electrolyte within a cavity 22 defined by the housing, enabling the reference electrode to provide a stable potential for comparison against the potential of the measuring electrode.

In the exemplary embodiment, the junction plug 24 defines a central passage that enables the measuring electrode 12 to extend beyond the liquid junction, to contact the target fluid. The junction plug includes a distal surface 52 that is exposed directly to the target fluid and a proximal surface 54 abutting the cross member 26(a).

The distal surface 52 of the junction plug 24 provides a relatively substantial surface area, enabling effective exposure to the target fluid and minimizing clogging of the plug. The junction plug is confined in the distal opening 34 defined by the housing.

In the exemplary embodiment, the junction plug 24 is formed of a unitary construction of porous ultra-high molecular weight polyethylene. Nonetheless, other material having suitable characteristics can be used. For example, effective materials include ground glass, ceramic, other porous plastics, and wood. The liquid junction can be formed of multiple components and materials.

In the exemplary embodiment, the first cross member 26(a) is disposed adjacent to the junction plug 20. The first aperture 26(a) is provided in a single prescribed region of the first cross member 24(a). With the cross member in place, ions traveling between the target fluid and the reference electrolyte must migrate axially through and transverse across the junction plug 20 to pass through the aperture of the cross member, resulting in an increased effective path length through the junction plug.

The first cross member 26(a) includes a stepped portion 56 disposed about the cylindrical bore 40 of the inner member and a planar portion 58 that extends from the stepped portion and positioned against the junction plug. The stepped portion and the junction plug define a void about the bore for receiving the o-ring 50 disposed about the measuring electrode.

As best seen in FIG. 1, the cross member 26(a) effectively substantially covers the proximal surface 54 of the junction plug. Preferably, the cross member covers between about 50 percent to about 98 percent of the proximal surface of the junction plug. In the exemplary embodiment, the cross member covers about 95 percent of the proximal surface. The aperture 28(a) is defined by the planar portion of the cross member. In the exemplary embodiment, the cross member defines a single circular aperture 28(a); however, other configurations can be used in other embodiments. For example, several apertures as well as other shapes, e.g., ring, rectangle, and so on, can be used. Moreover, in other embodiments, the cross member can be attached directly to the proximal surface of the cross member. Various aperture shapes can be combined in a single embodiment. Additional configurations are discussed in Applicants' co-pending U.S. patent application Ser. No. 11/533,989, filed Sep. 20, 2006, which is herein incorporated by reference for all purposes.

Figure 6:
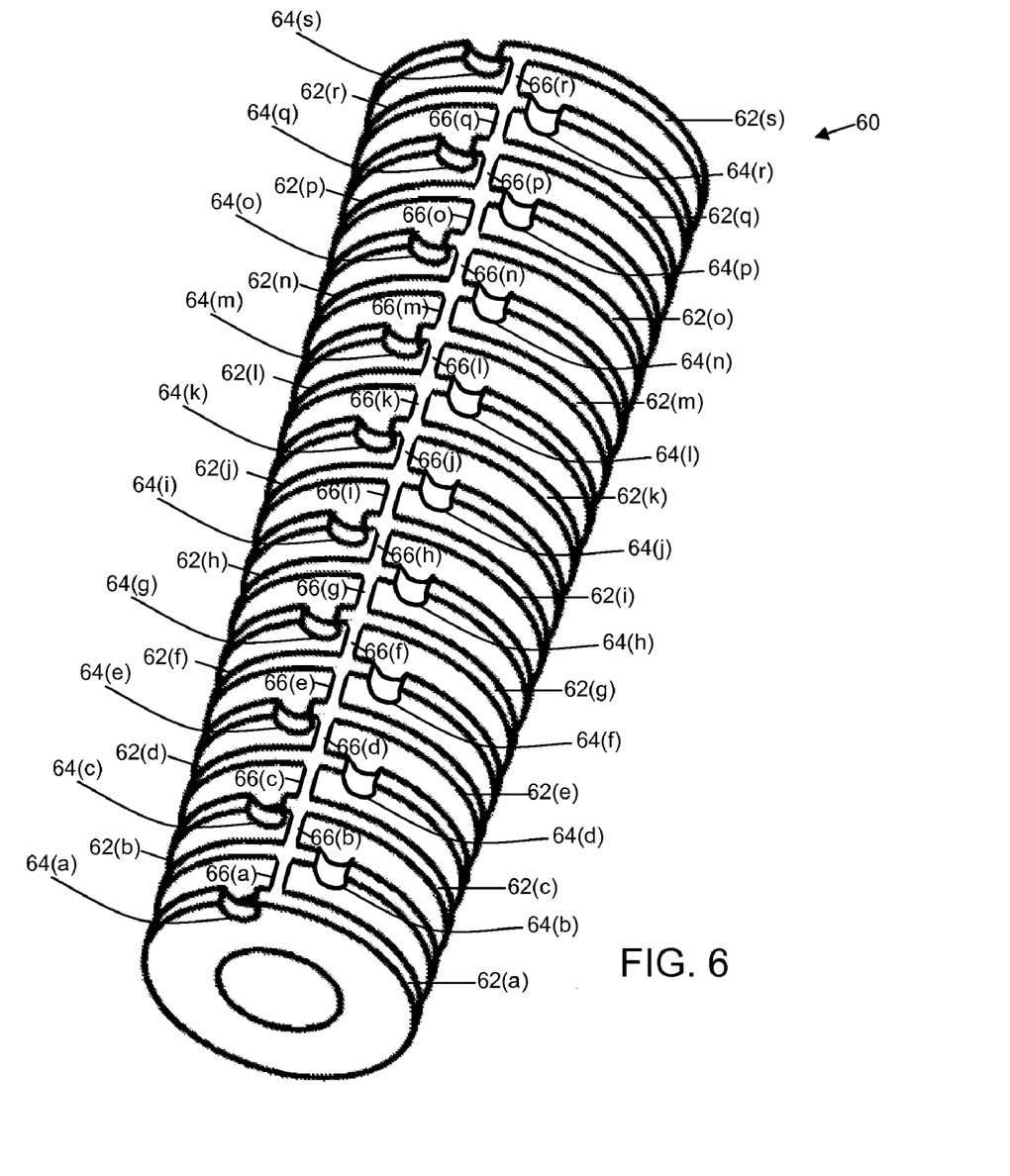
FIG. 6 is a perspective view, similar to FIG. 4, of an inner member of a second embodiment of an electrochemical sensor in accordance with the present invention, the inner member having vertical barriers disposed between adjacent cross members.

With reference to FIG. 6, an inner member 60 is shown, of a second embodiment of an electrochemical sensor in accordance with the invention. The second embodiment is generally similar to the first embodiment (sensor 10), with the primary difference being with the configuration of the inner member. The inner member 60 includes a plurality of cross members 62(a-s), each defining an aperture 64(a-s). The inner member further includes a plurality of barriers 66(a-r). Each barrier is disposed between adjacent cross members, resulting in a long tortuous path. In this embodiment, barriers are disposed between all cross members; although, few barriers can be used in other embodiments.

The apertures 64(a-s) of adjacent cross members are disposed on alternating sides of the corresponding barrier. For example, aperture 64(b) is disposed on a first side of the barrier, whereas aperture 64(c) is disposed on a second side of the barrier. The apertures 28(a-r) alternate in this manner between the proximal end and the distal end, requiring ionic flow between the target fluid and the reference electrode 14 to traverse laterally and longitudinally through the housing. On each level, the ions must travel substantially the full circumference of the housing between the adjacent apertures. As mentioned above, aperture plugs can be disposed in one or more of the apertures to retard contamination, while enabling ionic flow. Accordingly, the inner member aids in defining a long, tortuous flow path, or salt bridge, between the target fluid and the reference electrode, resulting in a high resistance factor for the sensor.

It should be appreciated from the foregoing that the present invention provides an electrochemical sensor that includes a housing having an outer wall, an axial bore circumscribed by the outer wall, and a barrier wall that aids in defining a reference cavity. The housing further including a plurality of cross members in spaced relation to one another disposed between the axial bore and the outer wall, each cross member defining an aperture. A junction plug is disposed at the distal end of the housing. The junction plug comprises a porous material that enables ionic flow through the junction plug. The sensor enables ionic communication between the target fluid and the reference electrode within the reference cavity passes through the apertures of the plurality of cross members. In this manner, the sensor provides generally a long, tortuous flow path, or salt bridge, between the target fluid and the reference electrode, resulting in a high resistance factor for the sensor.

Although the invention has been disclosed in detail with reference only to the exemplary embodiments, those skilled in the art will appreciate that various other embodiments can be provided without departing from the scope of the invention. Accordingly, the invention is defined only by the claims set forth below.

What is claimed is:

1. An electrochemical sensor, comprising:
    an elongated housing defining a longitudinal axis, the housing having a proximal end and a distal end configured to be exposed to a target fluid, the housing defining an interior configured to hold a reference electrolyte therein, the housing having
        an outer member axially aligned with the longitudinal axis of the housing, the outer member including an outer tubular wall substantially impermeable to ionic flow,
        an inner member formed of material substantially impermeable to ionic flow and disposed within the outer wall, the inner member including an inner tubular wall defining an axial bore axially aligned with the longitudinal axis of the housing,
        a plurality of cross members formed of material substantially impermeable to ionic flow, cooperatively defining the interior of the housing to include a plurality of levels that are axially aligned and stacked in spaced relationship to each other, wherein the plurality of levels are filled with the reference electrolyte, and
        a plurality of apertures defined by the housing, each aperture positioned to connect two adjacent levels of the plurality of levels such that the plurality of apertures enable and require ionic flow in the reference electrolyte to pass through each of the plurality of levels in a sequential manner between a distal level proximate to the distal end of the housing and a proximal level;
    a measuring electrode disposed in the axial bore and having a tip proximate to the distal end of the housing to be exposed to a target fluid;
    a reference electrode submerged in the reference electrolyte within the housing; and
    a junction plug comprising a porous material, the junction plug is disposed at the distal end of the housing to contact the target fluid.

2. An electrochemical sensor as defined in claim 1, wherein the housing is formed of molded plastic, including the outer member, the inner member, and the plurality of cross members.

3. An electrochemical sensor as defined in claim 1, wherein the plurality of apertures are positioned such that ionic flow must substantially travel at least 180 degrees about each level.

4. An electrochemical sensor as defined in claim 1, wherein the housing is configured and the plurality of apertures are positioned such that ionic flow must substantially circumscribe each level.

5. An electrochemical sensor as defined in claim 1, further comprising an upper seal positioned proximate to the proximal end of the housing, the upper seal configured to engage the inner wall and the outer wall.

6. An electrochemical sensor as defined in claim 1, wherein the junction plug and the housing are configured to enable ionic flow to pass between the target fluid and the distal level.

7. An electrochemical sensor as defined in claim 1, further comprising a cap disposed on the proximal end of the housing.

8. An electrochemical sensor as defined in claim 1, wherein the housing defines a reference chamber positioned within the housing proximate to the proximal level such that ionic flow passes from the proximal level to the reference chamber.

9. An electrochemical sensor as defined in claim 8, wherein the housing defines a single aperture between the distal level, and the reference chamber is disposed within the reference chamber.

10. An electrochemical sensor, comprising:
    an elongated housing defining a longitudinal axis, the housing having a proximal end and a distal end configured to be exposed to a target fluid, the housing defining an interior configured to hold a reference electrolyte therein, the housing having
        a plastic outer member axially aligned with the longitudinal axis of the housing, the outer member including an outer tubular wall substantially impermeable to ionic flow,
        a plastic inner member substantially impermeable to ionic flow and disposed within the outer wall, the inner member including an inner tubular wall defining an axial bore axially aligned with the longitudinal axis of the housing, and
        a plurality of cross members formed of material substantially impermeable to ionic flow, each cross member of the plurality of cross members circumscribing the inner tubular wall and extending to the outer wall, cooperatively defining the interior of the housing to include a plurality of levels that are axially aligned and stacked in spaced relationship to each other, wherein the plurality of levels are filled with the reference electrolyte,
        a plurality of apertures defined by the housing, each aperture positioned to connect two adjacent levels of the plurality of levels such that the plurality of apertures enable and require ionic flow in the reference electrolyte to pass through each of the plurality of levels in a sequential manner between a distal level proximate to the distal end of the housing and a proximal level, and
        a reference chamber defined by the housing, the reference chamber defined and positioned within the housing proximate to the proximal level such that ionic flow passes between the proximal level and the reference chamber;
    a measuring electrode disposed in the axial bore and having a tip proximate to the distal end of the housing to be exposed to a target fluid;
    a reference electrode submerged in the reference electrolyte within the reference chamber; and
    a junction plug comprising a porous material, the junction plug disposed at the distal end of the housing to contact the target fluid to facilitate ionic flow between the target fluid and the reference electrolyte.

11. An electrochemical sensor as defined in claim 10, wherein the plurality of apertures are positioned such that ionic flow must substantially travel at least 180 degrees about each level.

12. An electrochemical sensor as defined in claim 10, wherein the housing is configured and the plurality of apertures are positioned such that ionic flow must substantially circumscribe each level.

13. An electrochemical sensor as defined in claim 10, wherein the junction plug and the housing are configured to enable ionic flow to pass between the target fluid and the distal level.

14. An electrochemical sensor as defined in claim 10, further comprising an upper seal positioned proximate to the proximal end of the housing, the upper seal configured to engage the inner wall and the outer wall.

15. An electrochemical sensor as defined in claim 10, further comprising a cap disposed on the proximal end of the housing.

16. An electrochemical sensor as defined in claim 10, wherein the housing defines a single aperture between the distal level and the reference chamber.

17. An electrochemical sensor, comprising:
- an elongated housing defining a longitudinal axis, the housing having a proximal end and a distal end configured to be exposed to a target fluid, the housing defining an interior configured to hold a reference electrolyte therein, the housing having
  - an outer tubular wall axially aligned with the longitudinal axis of the housing and substantially impermeable to ionic flow,
  - an inner wall formed of material substantially impermeable to ionic flow disposed within the outer wall, the inner wall defining an axial bore,
  - a plurality of cross members formed of material substantially impermeable to ionic flow, each cross member of the plurality of cross members circumscribing the inner wall and extending to the outer wall, cooperatively defining the interior of the housing to include a plurality of levels that are axially aligned and stacked in spaced relationship to each other, wherein the plurality of levels are filled with the reference electrolyte, and
  - a plurality of apertures defined by the housing, each aperture positioned to connect two adjacent levels of the plurality of levels such that the plurality of apertures enable and require ionic flow in the reference electrolyte to pass through each of the plurality of levels in a sequential manner between a distal level proximate to the distal end of the housing and a proximal level;
- a measuring electrode disposed in the axial bore and having a tip proximate to the distal end of the housing to be exposed to a target fluid;
- a reference electrode submerged in the reference electrolyte within the housing; and
- a junction plug comprising a porous material, the junction plug is disposed at the distal end of the housing to contact the target fluid.

18. An electrochemical sensor as defined in claim 17, wherein the housing defines a reference chamber positioned within the housing proximate to the proximal level such that ionic flow passes from the proximal level to the reference chamber.

19. An electrochemical sensor as defined in claim 17, wherein the junction plug and the housing are configured to enable ionic flow to pass between the target fluid and the distal level.

20. An electrochemical sensor as defined in claim 17, wherein the plurality of apertures are positioned such that ionic flow must substantially travel at least 180 degrees about each level.

* * * * *